United States Patent

Lyons et al.

[11] Patent Number: 5,220,080
[45] Date of Patent: Jun. 15, 1993

[54] CHROMIA ON METAL OXIDE CATALYSTS FOR THE OXIDATION OF METHANE TO METHANOL

[75] Inventors: James E. Lyons, Wallingford; Vincent A. Durante, West Chester, both of Pa.; Darrell W. Walker, Visalia, Calif.

[73] Assignee: Sun Company, Inc. (R&M), Philadelphia, Pa.

[21] Appl. No.: 905,952

[22] Filed: Jun. 29, 1992

[51] Int. Cl.$^5$ ...................... C07C 29/50; C07C 31/04
[52] U.S. Cl. .................................. 568/910; 568/910.5
[58] Field of Search .............................. 568/910, 910.5

[56] References Cited

U.S. PATENT DOCUMENTS 2,020,671  11/1935  Dreyfus .................................. 568/910

Primary Examiner—Joseph E. Evans
Attorney, Agent, or Firm—Q. Todd Dickinson; Donald R. Johnson; Stephen T. Falk

[57] ABSTRACT

A process for the direct catalytic oxidation of methane to methanol comprises chromium chemically bound to the oxygen of a metal oxide catalytic support surface. The support may comprise silica, alumina, magnesia, titania, or zirconia.

22 Claims, No Drawings

CHROMIA ON METAL OXIDE CATALYSTS FOR THE OXIDATION OF METHANE TO METHANOL

BACKGROUND OF THE INVENTION

This invention relates to a method for the direct oxidation of light alkanes to form the corresponding alcohols; in particular, the direct catalytic oxidation of methane to methanol. The catalyst found to be useful in the method of this invention comprises chromium oxide chemically bonded to the oxygen atoms attached to a silicon, aluminum, titanium, or magnesium oxide support structure.

BACKGROUND OF THE ART

The ability to directly convert methane to methanol in economically satisfactory yields is an important goal of the oil and gas industry. Methane is an abundant material found world-wide, particularly in the form of natural gas. As a gas, it is difficult and costly to transport. Conversion to the liquid methanol allows for safer, more efficient transportation. In addition, methanol is a valuable commercial feedstock, an important ingredient in the production of reformulated motor fuels, and an environmentally compatible fuel in itself.

The conventional method for the catalytic conversion of methane to methanol involves a first reaction with water to produce synthesis gas, which is a mixture of carbon monoxide and hydrogen, followed by catalytic conversion of the synthesis gas to methanol. A direct, one-step oxidation of methane to methanol would be simpler, and economically and environmentally preferable.

Several catalytic and non-catalytic approaches to directly converting methane to methanol are known in the art. Among these are the following catalytic processes:

United Kingdom Pat. No. 1,244,001 discloses the oxidation of methane to methanol over a catalyst consisting of ($Mo_2O_3$) $Fe_2O_3$ on silica/alumina (25% $Al_2O_3$/75% $SiO_2$), sintered to 0.1 g/cm$^2$ at 1000° C., with 65% selectivity (moles Methanol/moles Product X 100) at 2.1% conversion. The temperature is 439° C. and the pressure 52 atmospheres. Temperatures, pressures and space rates in the process disclosed in this patent are 300°-550° C.; 5.150 atmospheres; and 20,000-50,000 hr$^{-1}$, respectively.

Eusuf, Sci. Res., Dacca (1969) Vol VI, Nos. 1,2, p.16, discloses the oxidation of methane to methanol over $CrO_3$/pumice. The reported results indicated 12% selectivity at 11% $O_2$ conversion. The reported 8.9% methane conversion is noted to most likely be an error as indicated by the reported carbon/oxygen balance. The actual conversion rate may have been far lower.

Further results on the chlorine-promoted oxidation of methane to methanol over $CrO_3$/pumice were reported in Eusuf, Bangl. J. Sci. Ind. Res. (1975) Vol. 10, Nos 1 2, pp. 135-141 ("Eusuf II"). Eusuf II discloses methane conversion as high as 7.3%, with yields of methanol on input methane basis as high as 46.4%. These results were observed at a temperature of 430° C., pressure at 1.5 atmospheres, and a contact time of 1.5 seconds. The reaction was run in the presence of $Cl_2$ at a volumetric ratio of 0.10, $Cl_2$:$CH_4$, indicating that there was more chlorine gas present than the amount of methane converted in the reaction.

Few, if any, catalysts currently exist, however, which will promote the direct oxidation of methane to methanol in commercially acceptable yield and selectivity. Durante et al, U.S. Pat. No. 4,918,249, assigned to Sun Company, Inc.(R&M), discloses oxidation of methane to methanol in 70% selectivity at 90% oxygen conversion over an iron framework-exchanged sodalite catalyst at temperatures around 415° C.

Most catalysts which contain oxidation-active transition metals do not produce significant amounts of methanol as oxidation product, but rather tend to combust methane to give carbon oxides and water at the elevated temperatures necessary for oxidation to occur. A catalyst which can oxidize methane to methanol at low temperatures could be very important in producing better selectivities by reducing unwanted carbon oxides. The process of the present invention succeeds in achieving higher conversions and methanol selectivities in the direct air oxidation of methane than any other process involving chromium-containing catalysts to date.

The process of the present invention involves direct air or oxygen conversion of methane to methanol. No promoter, such as chlorine gas, need be present, which has the added advantage of avoiding the production of chlorocarbon compounds and the creation of a highly corrosive chlorine-containing reaction system.

SUMMARY OF INVENTION

The present invention comprises a method for the direct conversion of light alkanes to alcohols, aldehydes and other oxidation products comprising contacting said light alkanes with oxidant in the presence of catalyst comprising a surface oxide chromate having the structure:

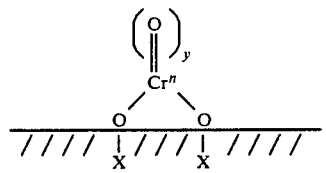

wherein multi-valent chromium moieties are chemically bound to oxygens of a catalytic support surface. The support surface is preferably an oxide of X, wherein X comprises an element selected from the group consisting of silicon, aluminum, magnesium, titanium and zirconium. More generally, any suitable solid metal may be used as the support surface. Alternatively, mixed metal oxides, such as silicoaluminates, and zeolites, may also be used. The oxidation state of the chromium, represented by n, is (VI), (IV), or (II) while the number of oxo groups, represented by y, is 2, or 0, respectively.

DETAILED DESCRIPTION OF INVENTION

The direct partial oxidation of methane to methanol has long been problematic. The goal is a desirable one because it holds promise for the utilization of vast methane reserves, principally in the form of natural gas, as methanol for clean-burning fuel and environmentally acceptable fuel additives. Low overall conversion rates and poor selectivity for methanol have previously rendered the process commercially impractical.

The process of the present invention employs a catalyst which comprises a chromia moiety chemically bound to a surface support structure. The silica supported catalysts of this invention, known as the Phillips Cr/silica catalyst, have previously been made for use as polymerization catalysts. Their use in the direct conversion of alkanes to alcohols, particularly the oxidation of methane to methanol, is novel.

Catalyst

The catalysts found to be useful in the present invention contain multi-valent chromium bound to oxygen atoms which comprise an integral part of the oxide support structure. The chromium moiety can be present in any of three oxidation states; specifically, chromium(VI)oxo, chromium(IV)oxo, and chromium(II).

According to the present invention, it is believed that in the course of alkane oxidation, the chromium in higher oxidation states is reduced by the alkane. Concurrently with the alkane oxidation, oxidant present in the system re. oxidizes the chromium to the higher oxidation state. Such regeneration of the chromium species can also be accomplished apart from the alkane oxidation reaction zone.

The catalysts found to be useful in the process of the present invention comprise surface oxide chromates in which chromium is chemically bound to the oxygen of a metal oxide catalytic support surface. The preferred surface oxide chromate catalysts of use in this invention comprise chromium di-oxo groups chemically bonded to a silicon oxide surface. These silylchromate catalysts in their most active state have the general structure:

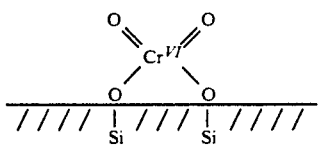

The chromia is believed to be supported on silica in such a way that some or all of the chromia is bonded to surface oxygens. The chromia initially has chromium in oxidation state VI. Chromium(VI) has two oxo oxygens as indicated in the structure above.

One method of making the Phillips Cr/silica catalysts of this invention is taught in McDaniel and Welch, J. Catal. (1983) 82, 98–118, which is incorporated herein by reference. According to this method, chromia is believed to be deposited on silica such that all or part of the chromia is chromium(VI)di-oxo bound to oxygen atoms of the silica support surface.

Alternative embodiments of the catalyst useful in the process of this invention comprise chromia chemically bonded to a surface support comprising an oxide of aluminum, magnesium, titanium, zirconium, or other suitable solid metal, or mixtures thereof, such as silicoaluminates. In another embodiment the support surface may comprise zeolite. These catalysts can have similar general structures to that depicted above in which the silicon in the oxide surface is replaced by one of the named metals. Similarly to the silica supported catalysts described above, these catalysts can be prepared in generally the same manner as the silica-supported catalysts described above, but with a surface support comprising alumina, magnesia, titania, zirconia, other suitable solid metals oxides, or mixed metal oxides.

The concentration of chromia in the silylchromate catalyst ranges from 0.1 to 1.0 weight percent, preferably 0.5 to 0.6 weight percent, and more preferably 0.6 weight percent. It is believed that approximately 0.6 weight percent chromium provides the most efficient distribution of active chromia moieties on the silica support.

Feedstock

The preferred feedstock for the process of the invention is light alkane, or a mixture of light alkanes, having from 1 to 4 carbon atoms in the molecule. These light alkanes may include methane, ethane, propane, n-butane and isobutane and gaseous mixtures such as natural gas. Among the products of the oxidation are the alcohols corresponding to the particular alkanes which are present in the feedstock.

Reaction Zone

The process of the present invention has been carried out in a glass-lined, tubular reactor. Other conventional reactor configurations can be used as well, which are known to those skilled in the art. The catalyst may be maintained within the reaction zone in a variety of reactor bed configurations including fixed beds, fluid beds, ebullating beds and moving beds.

Reaction Conditions

The process of the present invention, particularly the oxidation of methane to methanol, is preferentially carried out in the vapor phase.

In one embodiment, the process is carried out in a fixed bed reaction zone at temperatures between 250° and 550° C., preferably between 350° and 450° C., and more preferably between 400° and 430° C. Pressure in the reaction zone is maintained between 100 and 1500 psig, preferably 700 to 900 psig, and the gas hourly space velocity (GHSV) is in the range of 200 to 25000 hr$^{-1}$, preferably 500 to 12000 hr$^{-1}$. Air or molecular oxygen are the preferred oxidants.

When air is used as the oxidant, light alkane to air mixtures outside the explosive region have been found to be effective. Particularly, oxygen-lean light alkane to air mixtures outside the explosive limit are effective. Mixtures in the neighborhood of 3:1 alkane to air are preferred for laboratory operations. When oxygen is used, an alkane to oxygen ratio of about 14:1 is effective.

Without intending to be bound by a particular theory, it is believed that the mechanism of the alkane oxidation reaction involves reduction of the chromium(VI)di-oxo group to chromium(IV)oxo and further to chromium(II). In the presence of air or oxygen, the catalyst itself is re-oxidized to its hexavalent state.

According to one embodiment of the present invention, surface silylchromates are used as catalysts to obtain improved results for the oxidation of alkanes, such as methane, to alcohols. Specifically, the process of this invention achieves greater selectivities and conversions than prior art processes using chromium catalysts for the airoxidation of methane.

The following example illustrates the invention:

EXAMPLE

The Table shows the results of a series of oxidation reactions comparing the activity of three formulations of the chromia on silica catalyst as used in the process of the invention. In these oxidation reactions, the ratio of methane to air was 3:1, and the pressure was 800 psig. The vapor phase reaction was conducted continuously over 1.0 cc of catalyst. The results are averages of four samples taken at one hour intervals after a two-hour equilibration period. The reaction runs were performed at various temperatures and flow rates as indicated.

The Table sets forth the percentage of oxygen converted, the percentage of methane converted, the rate of methanol production (in mmoles/hr), and the methanol selectivity of the various reactions. As between the three chromia on silica catalysts, the results indicate that the catalysts containing 0.5 and 0.6 weight percent chromia showed enhanced activity. At 0.6 wt. % chromia, 5.1% methane conversion with 37% methanol selectivity was achieved.

The catalysts employed in the present invention are active at temperatures and pressures below those of previously disclosed processes using chromia catalysts.

TABLE
OXIDATION OF METHANE OVER CHROMIA ON SILICA[a]

| Catalyst | Temp. (°C.) | Gas Flow (ml/min) | $O_2$ Conv. % | $CH_4$ Conv. % | $CH_3OH$ Produced (mmoles/hr) | $CH_3OH$ Selectivity % |
|---|---|---|---|---|---|---|
| 0.5% $CrO_3/SiO_2$ | 390 | 800 | 15 | 0.6 | 3.9 | 41 |
| " | 400 | 800 | 29 | 1.8 | 10.9 | 38 |
| " | 400 | 200 | 70 | 3.9 | 18.8 | 41 |
| " | 410 | 800 | 38 | 2.0 | 11.8 | 38 |
| " | 420[b] | 800 | 90 | 5.4 | 18.5 | 22 |
| " | 350 | 100 | 15 | 0.4 | 0.3 | 34 |
| " | 300 | 50 | 9 | 0.1–0.2 | <0.1 | 42 |
| 0.6% $CRO_3/SiO_2$ | 390 | 100 | 56 | 3.1 | 2.0 | 32 |
| " | 410 | 95 | 93 | 4.8 | 3.1 | 32 |
| " | 408 | 200 | 99 | 5.0 | 7.3 | 35 |
| " | 418 | 390 | 93 | 5.1 | 15.5 | 37 |
| " | 411 | 800 | 59 | 2.8 | 18.8 | 40 |
| 3% $CrO_3/SiO_2$ | 430 | 800 | 22 | 0.7 | 4.6 | 41 |
| " | 400 | 400 | 18 | 0.7 | 2.5 | 43 |
| " | 400 | 200 | 22 | 0.7 | 0.9 | 33 |
| " | 375 | 200 | 22 | 0.9 | 1.3 | 38 |
| " | 350 | 100 | 22 | 0.9 | 0.3 | 16 |
| " | 300 | 50 | 18 | 0.4 | 0.02 | 4 |

[a]Continuous oxidation of methane (800 psig, 3:1 methane:air ratio) over 1.0 cc of catalyst top-loaded into a fully heated 4 cc quartz-lined tubular reactor. Results reported are average of four samples taken at one hour intervals after a two-hour equilibration period.
[b]Exotherm caused internal temperature of 442° C. during reaction.

What is claimed is:

1. A method for the direct conversion of light alkanes to alcohols comprising contacting said light alkanes with an oxidant in the presence of catalyst comprising a surface oxide chromate in which chromium is chemically bound to oxygen of a metal oxide support surface.

2. The method as claimed in claim 1, wherein said catalyst comprises the structure:

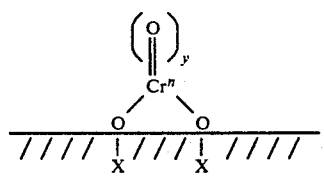

wherein valence n is (VI), (IV), or (II) and y is 2, 1, or 0, respectively; and wherein said chromium is chemically bound to oxygen atoms of said metal oxide support surface comprising oxide of X, wherein X is selected from the group consisting of silicon, aluminum, magnesium, titanium, zirconium and mixtures thereof.

3. The method as claimed in claim 2, wherein said chromium exists in the form of a hexavalent chromium di-oxo moiety; namely, chromium (VI) oxide.

4. The method as claimed in claim 2, wherein X comprises silicon.

5. The method as claimed in claim 4, wherein the chromium concentration in said catalyst is in the range of approximately 0.1 to 1.0 weight percent.

6. The method as claimed in claim 5, wherein said concentration is in the range of approximately 0.5 to 0.6 weight percent.

7. The method as claimed in claim 6, wherein said concentration is 0.6 weight percent.

8. The method as claimed in claim 1, wherein said light alkane comprises compounds selected from the group consisting of methane, ethane, propane, n-butane, isobutane and natural gas or mixtures thereof.

9. The method as claimed in claim 8, wherein said light alkane comprises methane.

10. The method as claimed in claim 1, wherein said oxidant is selected from the group consisting of oxygen, air, and mixtures thereof.

11. The method as claimed in claim 10, wherein said oxidant is oxygen.

12. The method as claimed in claim 10, wherein said oxidant is air.

13. The method as claimed in claim 1, wherein said conversion is carried out at a gas hourly space velocity (GHSV) in the range of approximately 200 to 25000 per hour ($hr^{-1}$).

14. The method as claimed in claim 13, wherein said GHSV is in the range of approximately 500 to 12000 $hr^{-1}$.

15. The method as claimed in claim 1, wherein said conversion is carried out at a temperature in the range of approximately 250° to 550° C.

16. The method as claimed in claim 15, wherein said temperature is in the range of approximately 300° to 450° C.

17. The method as claimed in claim 16, wherein said temperature is in the range of approximately 400° to 430° C.

18. The method as claimed in claim 1, wherein said conversion is carried out at a pressure in the range of approximately 100 to 1500 psig.

19. The method as claimed in claim 18, wherein said pressure is in the range of approximately 700 to 900 psig.

20. The method as claimed in claim 1, wherein said catalyst is maintained in a reactor bed selected from the group consisting of fixed, fluid, ebullating, and moving beds.

21. The method as claimed in claim 20, wherein said reactor bed is fixed.

22. A method for the direct conversion of light alkanes to alcohols comprising contacting said light alkanes with an oxidant in the presence of catalyst comprising a surface oxide chromate in which chromium is chemically bound to a zeolite, wherein said catalyst comprises the structure:

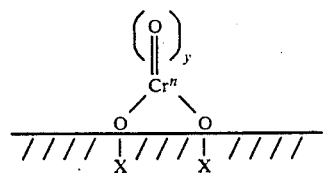

wherein valence n is (VI), (IV), or (II) and y is 2, 1, or 0, respectively; and wherein X is zeolite.

* * * * *